United States Patent [19]
Bernhardt et al.

[11] Patent Number: 5,591,166
[45] Date of Patent: Jan. 7, 1997

[54] MULTI ANGLE BONE BOLT

[75] Inventors: Andrew Bernhardt, Cordova; Matthew M. Morrison, Memphis, both of Tenn.

[73] Assignee: Smith & Nephew Richards, Inc., Memphis, Tenn.

[21] Appl. No.: 411,532

[22] Filed: Mar. 27, 1995

[51] Int. Cl.⁶ .................................................. A61B 17/56
[52] U.S. Cl. .......................... 606/61; 606/60; 606/72; 606/73; 606/69
[58] Field of Search ................... 606/61, 60, 73, 606/72, 69; 411/383, 388, 389, 397

[56] References Cited

U.S. PATENT DOCUMENTS

| | | | |
|---|---|---|---|
| 4,946,458 | 8/1990 | Harms et al. | 606/61 |
| 5,129,899 | 7/1992 | Small et al. | 606/61 |
| 5,176,679 | 1/1993 | Lin | 606/61 |
| 5,196,014 | 3/1993 | Lin | 606/61 |
| 5,330,474 | 7/1994 | Lin | 606/61 |

*Primary Examiner*—Michael Powell Buiz
*Assistant Examiner*—Mark S. Leonardo
*Attorney, Agent, or Firm*—Pravel, Hewitt, Kimball & Krieger

[57] ABSTRACT

An orthopedic bone bolt and bone plate construct comprising a bone plate member and a series of fasteners. The bone plate member has at least one open portions, with the open portions allowing placement of a series of fasteners therethrough at spaced apart positions along a length of the open portions. The series of fasteners are attachable to the plate member at the open portions, with at least one of the fasteners including a multi-angle fastener having a pair of fastener sections configured to be angled relative to one another. The multi-angle fastener comprising; an upper section having a central longitudinal axis and an outer surface; a lower section having a central longitudinal axis and an outer surface with a threaded portion configured to be surgically implantable into a patient's bone tissue and a joint for connecting the upper and lower sections together. The joint including corresponding mating surfaces configured to articulate with each other sufficiently to allow the upper and lower sections to angle relative to one another.

26 Claims, 4 Drawing Sheets

MULTI ANGLE BONE BOLT

SPECIFICATION

FIELD OF THE INVENTION

The present invention relates to orthopedic surgery and more particularly to an improved fixation apparatus for placing a series of bone bolts in the bones of a human patient wherein the bone bolts are multi-angled so as to accommodate the differences in position of adjacent bolts implanted in a series.

BACKGROUND OF THE INVENTION

There are a number of surgical procedures which require the fixation of bones such as spinal fixation of portions of the spine with respect to one another or fixation of bone fragments as a result of trauma. Typically, bone bolts or screws and bone plates or spinal rods are employed in the fixation of bones wherein the bone bolts or screws are implanted in a surgical procedure involving the formation of a series of surgical openings in adjacent portions of the spine or along a bone, for implanting the threaded bone bolts or screws. Connective structures such as rods or plates extend between the various spine members or bone fragments and are connected to the implanted bolts or screws with connector devices.

A U.S. Pat. No. 4,369,769 to Edwards shows a spinal fixation system using elongated rods to bridge across various portions of the spine. In the Edwards '769 patent, a spinal fixation device is provided in which sleeves or spacers are placed over and around spinal rods in order to obtain a better reduction of spinal fractures or spinal deformities. These sleeves can be made into various thicknesses so that the surgeon can obtain optimum fixation in each case.

Use of bone screws in connecting rods is also seen in the Ulrich et al. U.S. Pat. No. 4,433,677 entitled "Implantable Splint for Correction of Lumbosacral Spondylodesis." In the Ulrich patent, a spinal distraction splint has two like anchor screws extending along respective longitudinal screw axes and adapted to be anchored in the pelvis with the axes crossing. Each of the screws has a head formed with a transverse open recess centered on respective transverse axis and with an angular array of teeth centered on and angularly spaced about the respective transverse axis.

A U.S. Pat. No. 4,611,581 to Steffee entitled "Apparatus for Straightening Spinal Columns" provides an apparatus to reduce the extent of displacement between adjacent vertebrae and a person's spinal column and to subsequently maintain the vertebrae in a reduced displacement relationship. When the apparatus is to be installed, holes are formed in the displaced vertebrae and in vertebrae on opposite sides of the displaced vertebrae. Force transmitting members (bone bolts) are mounted in the holes in the vertebrae. A spinal plate is then positioned on the spinal column with the bone bolts extending outwardly through the slots in the spinal plate. Nuts are tightened on the bone bolt members connected with vertebrae on opposite sides of the displaced vertebrae to anchor the spinal plate in place. A nut on the extending bone bolt is then tightened to hold the displaced vertebrae in the desired position. Connectors for attaching the rods or plates to vertebrae of a spinal column are known in the art, for example such as those described in U.S. Pat. Nos. 5,209,752 and 5,296,014.

When doctors use a plurality of bone bolts implanted in a series of bolts, and desire a connection of the series, it is frequently difficult to make a tight connection because of the non-alignment of the series. For example, in a spinal construct where bone bolts are placed in several adjacent vertebral pedicles, the adjacent bone bolts will almost never align themselves such that a plate or rod may be connected to them. The adjacent bone screws are usually independently located with respect to each other in three dimensional space, which creates an offset distance of some kind between the bolt and the plate/rod connection. The offset problem has been addressed by providing connectors that accommodate the differences of the adjacent bolts implanted in a series. However, there is a limit to the adjustability of the currently available connectors when used with traditional bone bolts and bone screws.

In order to accommodate the differing spinal vertebrae of many patients and to provide a fixation system in which a series of implanted bone bolts can be aligned so as to provide adjustment for the three dimensional differences in the implanted bolts, a medical device such as a multi-angle bone bolt is needed that allows for variability in both placement and angulation of upper and lower portions of the bolt in order to provide an effective bone fixation system.

A multi-angle bone bolt is also needed for use in any bone fixation system in which uneven bone portions are connected to a connecting member where angulation of upper and lower portions of the bolt will provide a more effective and secure bone fixation system.

SUMMARY OF THE INVENTION

The object of the present invention is to provide an orthopedic bone bolt and bone plate or rod construct having a multi-angle bone bolt that provides a two section bolt in which the sections can be independently aligned in relation to one another. In one embodiment, the orthopedic construct includes a bone plate member having at least one open portion or a plurality of open portions with the open portions allowing placement of a series of fasteners therethrough at spaced apart positions along the length of the open portions. The series of fasteners are attachable to the plate member at the open portions with at least one of the fasteners including a multi-angle fastener having a pair of fastener sections configured to be angled relative to one another.

The multi-angle fastener includes an upper section having a central longitudinal axis and an outer surface, and a lower section having a central longitudinal axis and an outer surface with a threaded portion configured to be surgically implantable into a patient's bone tissue. The multi-angle fastener has a joint for connecting the upper and lower sections together with the joint having corresponding mating surfaces configured to articulate with each other sufficiently to allow the upper and lower sections to angle and rotate relative to one another.

In a second embodiment, the construct includes a spinal rod rather than a plate, in which the rod is connected to a plurality of rod/bolt connectors and the multi-angle fasteners are attached to the connectors. Thus, the multi-angle fastener of the present invention provides for independent alignment of each fastener which allows for more obtainable connections between a plurality of bolts implanted in a series and connected to a bone plate or connectors spaced along a spinal rod.

Another object of the invention is to provide a multi-angle fastener having two sections in which the sections can be independently aligned in relation to one another for use in any bone fixation system where uneven bone portions are being surgically fixed with a plate or other connecting member.

BRIEF DESCRIPTION OF THE DRAWINGS

For a further understanding of the nature and objects of the present invention, reference should be made to the following detailed description taken in conjunction with the accompanying drawings, in which like parts are given reference numerals and wherein.

DETAILED DESCRIPTION OF THE PREFERRED EMBODIMENT

Figure 1:
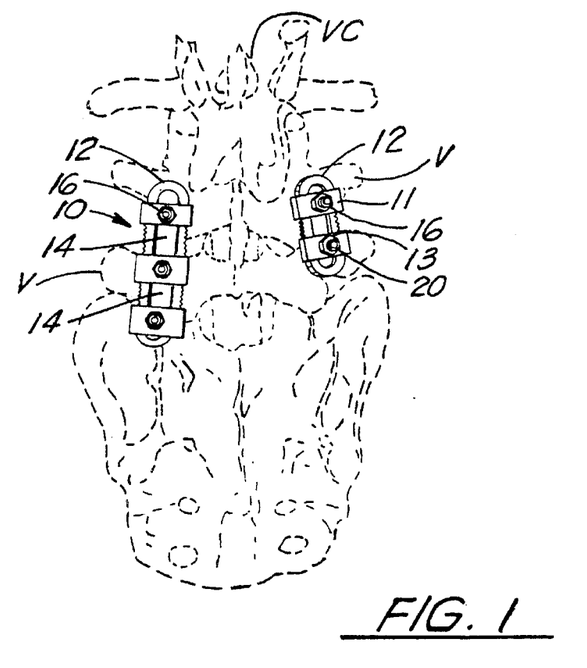
FIG. 1 is a schematic view illustrating the construct of the present invention implanted in a human patient as a spinal plate fixation system.

FIG. 1 shows an orthopedic bone bolt and bone plate construct of the present invention designated generally by numeral 10 implanted in a portion of a vertebral column VC of a human patient. The construct 10 includes a bone plate member 12 having a slot or a plurality of open portions 14 and a series of fasteners 16 such as non-articulating bone bolts known in the art. Open portions 14 are configured so as to allow placement of a series of fasteners 16 therethrough at spaced apart positions along a length of the slot or open portions 14 of the bone plate member 12, as shown in FIG. 1. The series of fasteners 16 attach to the plate member 12 through connecting devices known in the art, such as washers 11 and nuts 13, as illustrated in FIG. 1.

Figure 3:
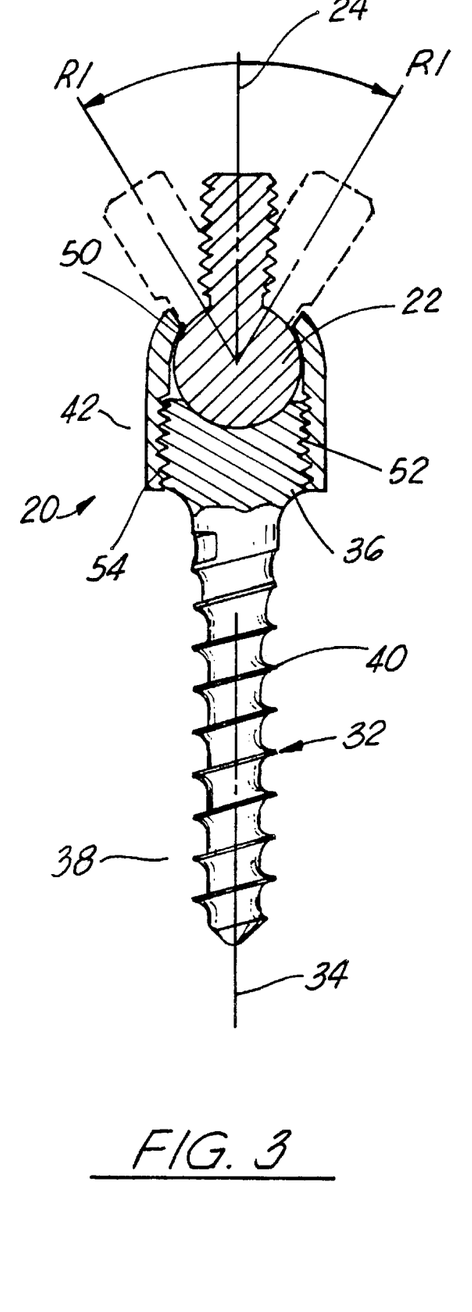
FIG. 3 is a partial cross sectional view of a fastener used in the construct of the present invention.
Figure 4:
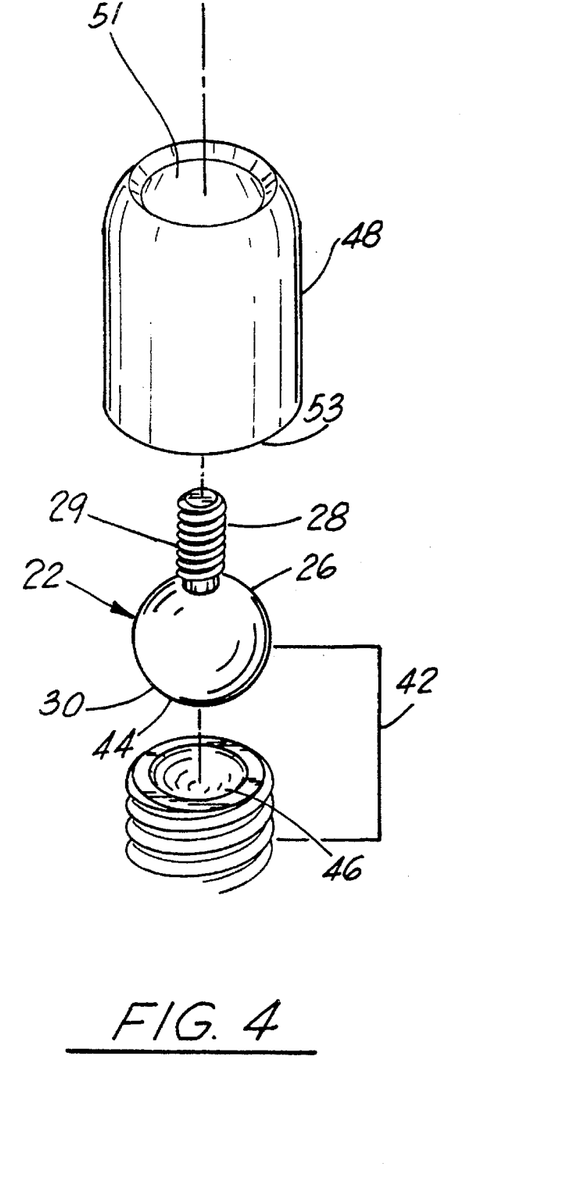
FIG. 4 is an exploded perspective view of a portion of the fastener of the present invention shown in FIG. 3.
Figure 5:
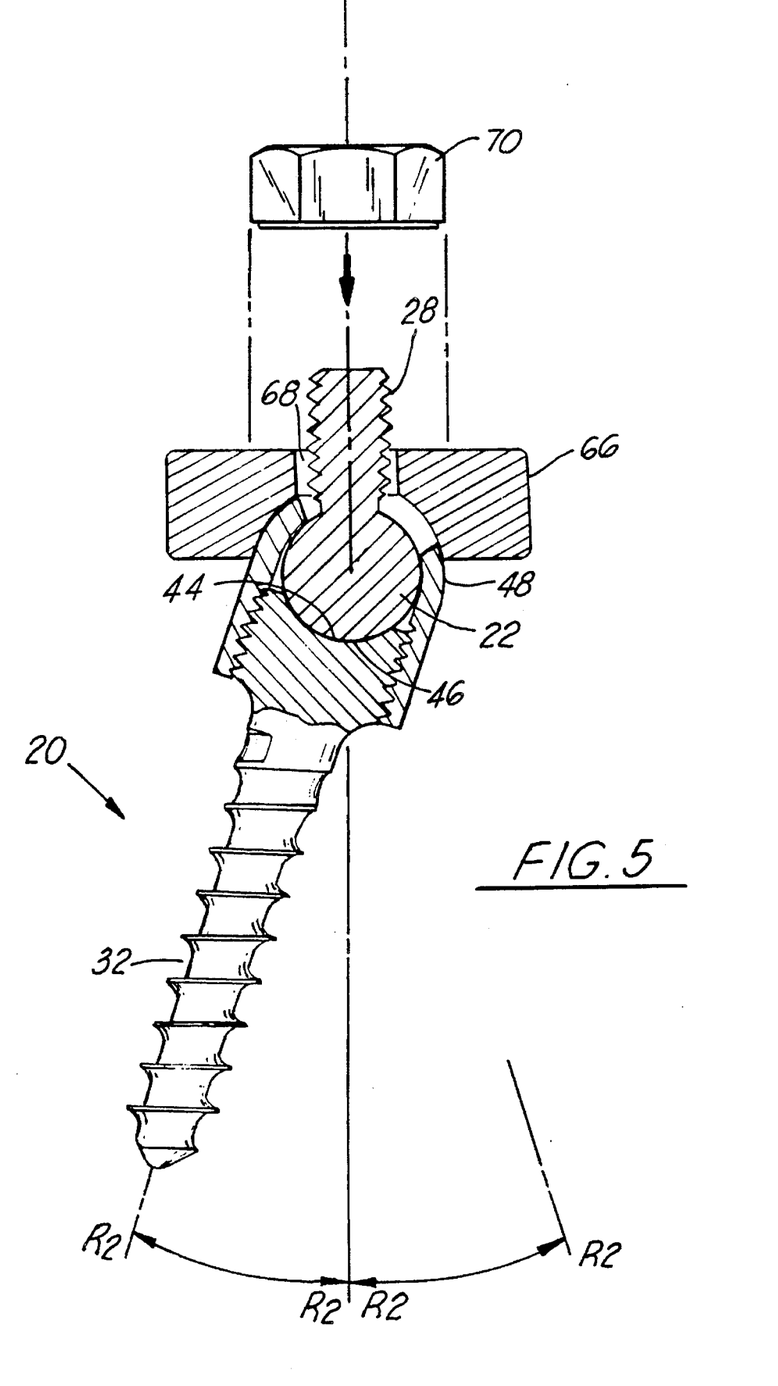
FIG. 5 is a partial sectional elevational view of a connector and nut in use with the present invention as seen in FIG. 3.

In construct 10, at least one of the fasteners 16 is a multi-angle fastener 20, having an upper section 22 and a lower section 32. As shown in FIGS. 3, 4 and 5, upper section 22 includes a central longitudinal axis 24, an outer surface 26 that is generally spherical in shape, and a proximal end 27 and a distal end 30. Upper section 22 includes a projection 28 at the proximal end 27 that is generally cylindrical in shape and has a threaded outer surface 29. Projection 28 is configured to engage a nut such as nut 13 illustrated in FIG. 1. Lower section 32 has a central longitudinal axis 34, a proximal end 36 that is generally cylindrical in shape, and a distal shaft end 38. Shaft end 38 has bone attachment means, such as a threaded outer surface 40, configured to be surgically implantable into a patient's bone tissue. The proximal end 36 of lower section 32 includes threading 54 on a portion of its outer surface. section 22 has a mating surface 44 at its distal end 30 and lower section 32 has a corresponding mating surface 46 at its proximal end 36. Mating surfaces 44, 46 form at joint 42 a ball and socket type joint, as illustrated in FIGS. 3, 4 and 5. Mating surface 44 is configured so as to form the convex shape of the ball portion of joint 42 and mating surface 46 is configured so as to form the concave shape of the socket portion of joint 42. Mating surfaces 44, 46 articulate with each other sufficiently to allow upper and lower sections 22, 32 to angle and rotate relative to one another in a range of between about 20–70° in relation to the central longitudinal axes 24, 34 of the upper and lower sections 22, 32. The range of rotation of upper section 22 is illustrated in FIG. 3 as R1—R1 and the range of rotation of lower section 32 is illustrated in FIG. 5 as R2—R2 which are identical ranges of motion.

A sleeve 48 surrounds joint 42 for holding together the upper and lower sections 22, 32. Sleeve 48 is generally cylindrical in shape and has an inner surface 50 with threading 52 on a portion of the inner surface 50. Sleeve 48 has an top through opening 51 and a bottom through opening 53. Fastener 20 is assembled by inserting the projection 28 of upper section 22 through opening 51 of sleeve 48 with the upper section 22 fitting within the conforming inner surface 50 of sleeve 48. Sleeve 48 is then placed over the proximal end 36 of the lower section 32 with the mating surfaces 44, 46 of the upper and lower sections 22, 32 forming the ball and socket joint 42. Sleeve 48 is tightened in place by screwing the sleeve 48 over the threaded outer surface 54 of the proximal end 36 of lower section 32 whereby the sleeve threading 52 engages and cooperates with the threaded outer surface 54 of lower section 32. The degree of rotation available after assembly depends upon how tightly sleeve 48 is threaded on the lower section 32. However, the ball and socket joint 42 will eventually loosen and allow the full range of motion at the joint 42.

When construct 10 is implanted in a patient's bone tissue, the multi-angle fastener 20 will provide a semi-rigid connection between the implanted multi-angle fastener 20 and the bone plate 12 or rod due to the articulation of joint 42. Upper and lower sections 22, 32 can thus be independently aligned relative to one another so as to provide a more secure and obtainable connection with the construct 10 which includes bone plate 12 and the series of implanted fasteners 16 and 20.

Figures 6, 7:
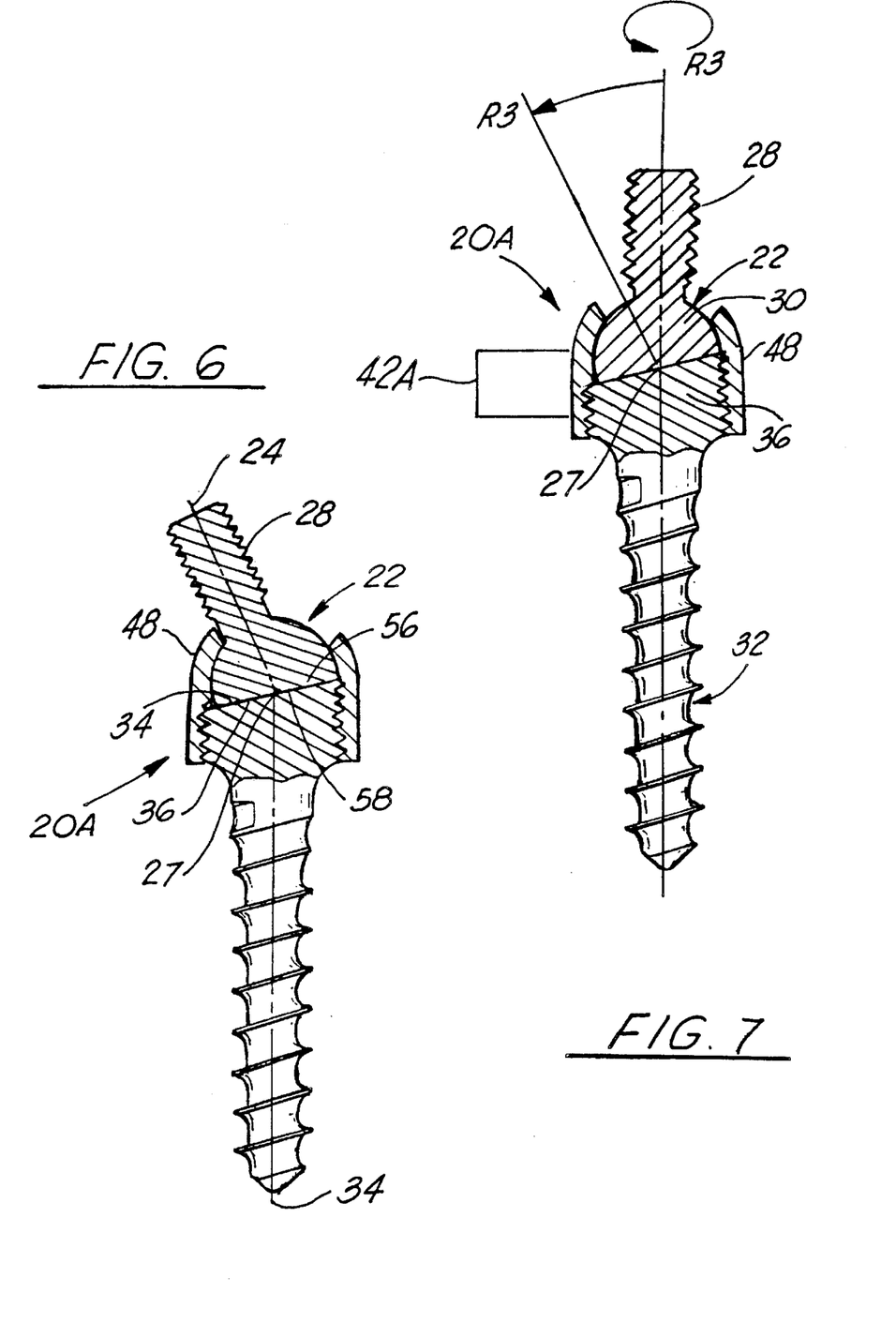
FIG. 6 is a partial cross sectional elevational view of a second fastener used in the construct of the present invention.
FIG. 7 is a partial cross sectional elevational view of the fastener in FIG. 6 showing range of rotational movement.

In a second embodiment of the invention, a fastener 20A is provided with a different kind of joint 42A that articulates within sleeve 48, as shown in FIGS. 6 and 7. In fastener 20A the upper section 22 has a flat mating surface 56 at its distal end 30 which is angled between about 55–80° relative to the central longitudinal axis 24 of the upper section 22. A corresponding flat mating surface 58 is on the proximal end 36 of lower section 32 and is also angled between about 55–80° relative to the central longitudinal axis 34 of lower section 32. The angle of the mating surfaces 56, 58 is such that the center longitudinal axes 24, 34 of the upper and lower sections 22, 32 remains coincident during rotation at center-point 27. Joint 42A of the multi-angle fastener 20A is configured to allow for rotation, in a conical pattern, of the upper and lower sections 22, 32 relative to one another in a range of between about 20–70° in relation to the central longitudinal axes 24, 34 of upper and lower sections 22, 32. The range of rotation is illustrated as R3—R3 in FIG. 7. All of the other features of fastener 20A are the same as those found in fastener 20.

When implanted in a patient's bone tissue as part of construct 10, the multi-angle fastener 20A will provide a rigid connection between the implanted multi-angle fastener 20 and the bone plate 12 because of the flat mating surfaces 56, 58 of joint 42A rather than the semi-rigid connection of fastener 20. Thus, upper and lower sections 22, 32 can be independently aligned relative to one another so as to provide a more secure and obtainable connection with construct 10 which includes bone plate 12 and the series of implanted fasteners 16 and 20A.

Figure 2:
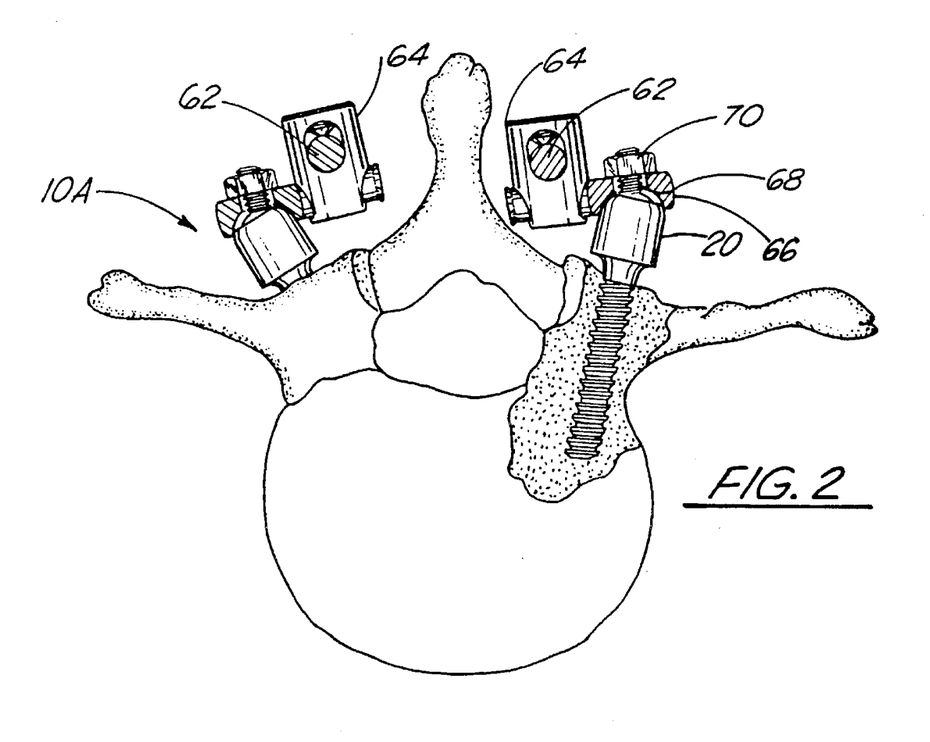
FIG. 2 is a fragmentary partial cross sectional view of a vertebrae illustrating the construct of the present invention implanted in a human patient as a spinal rod fixation system.

The multi-angle fasteners 20, 20A can also be used when an orthopedic bone bolt and spinal rod construct 10A is used in place of the construct 10, as shown in FIGS. 2 and 5. A spinal rod 62 is connected to a plurality of rod/bolt connectors 64 of a type known in the art and illustrated in FIG. 2. Rod/bolt connector 64 has a leg portion 66 with an opening 68 which allows placement of the threaded projection 28 of the upper section 22 therethrough. A nut 70, configured to mate with the threaded projection 28 is placed over projection 28 and tightened down on leg portion 66 in order to secure the multi-angle fastener 20 or 20A to the rod/bolt connector 64.

When implanted in a patient's bone tissue, the multi-angle fasteners 20, 20A provide a more secure and obtainable connection for construct 10 (bone plate) and construct 10A (spinal rod and connectors) when the fasteners are implanted in a series. The multi-angle fasteners 20, 20A provide a two section bolt in which the sections can articulate in relation to one another, thus allowing for independent alignment of the bolt sections when implanted in a patient's bone tissue.

Multi-angle fasteners 20, 20A can also be used in any bone fixation system in which bone portions needed to be fixed to a connecting member in order to hold the bone portions together. For example, a single multi-angle fastener 20 or 20A can be used in attaching external fixation rings (Illizariv), external fixation posts, or trauma related external or internal fixation structures to bone.

It should be understood that there can be improvements and modifications made to the embodiments of the invention described in detail above without departing from the spirit or scope of the invention, as set forth in the accompanying claims.

What is claimed is:

1. An orthopedic bone bolt and bone plate construct comprising:
   a) a bone plate member having at least one open portion, each open portion allowing placement of a series of fasteners therethrough at spaced apart positions along a length of each open portion;
   b) a series of fasteners attachable to said plate member at said at least one open portion, at least one of said fasteners including a multi-angle fastener having a pair of fastener sections configured to be angled relative to one another;
   c) said multi-angle fastener comprising;
      an upper section having a central longitudinal axis, an externally threaded projection and an outer surface;
      a lower section having a central longitudinal axis and an outer surface having bone attachment means configured to be surgically implantable into a patient's bone tissue;
      joint means for connecting the upper and lower sections together, said joint means including corresponding mating surfaces configured to articulate with each other sufficiently to allow the upper and lower sections to angle relative to one another.

2. The construct of claim 1, wherein the mating surfaces include corresponding concave and convex surfaces shaped to allow for a rotational movement of the upper and lower sections, with the corresponding concave and convex surfaces providing a semi-rigid connection within the multi-angle fastener.

3. The construct of claim 2, wherein the rotational movement of the upper and lower sections allows for a range on angulation in a range of about between 20–70 degrees relative to the central longitudinal axes of the upper and lower sections.

4. The construct of claim 1, wherein the mating surfaces include a pair of flat surfaces, said flat surfaces each forming an angle with the axes of the upper and lower sections when said axes are aligned, said flat surfaces angled to allow for a rotational movement of the upper and lower sections, with the pair of angled flat surfaces providing a rigid connection within the multi-angle fastener.

5. The construct of claim 4, wherein the flat surfaces are angled to allow for rotational movement in a range of about between 20–70 degrees relative to the central longitudinal axes of the upper and lower sections.

6. The construct of claim 1, further including a sleeve configured to surround the joint means for holding together the upper and lower sections at the joint means.

7. The construct of claim 6, wherein the sleeve is cylindrical in shape and includes an inner surface with threading on a portion of the inner surface, said sleeve threading engaging a threaded portion on the outer surface of the lower section of the fastener.

8. The construct of claim 1, wherein the series of fasteners includes at least two multi-angle fasteners.

9. The construct of claim 1, wherein the series of fasteners includes at least one bone bolt not capable of articulation.

10. An orthopedic bone bolt and spinal rod construct comprising:
    a) a spinal rod connected to a plurality of rod/bolt connectors, each connector having an open portion with each open portion allowing placement of a fastener therethrough, the connectors being at spaced apart positions along a length of the spinal rod;
    b) a series of fasteners attachable to each of said connectors at each said connector open portion, at least one of said fasteners including a multi-angle fastener having a pair of fastener sections configured to be angled relative to one another;
    c) said multi-angle fastener comprising;
       an upper section having a central longitudinal axis, an externally threaded projection and an outer surface;
       a lower section having a central longitudinal axis and an outer surface having bone attachment means configured to be surgically implantable into a patient's bone tissue;
       joint means for connecting the upper and lower sections together, said joint means including corresponding mating surfaces configured to articulate with each other sufficiently to allow the upper and lower sections to angle relative to one another.

11. The construct of claim 10, wherein the mating surfaces include corresponding concave and convex surfaces shaped to allow for a rotational movement of the upper and lower sections, with the corresponding concave and convex surfaces providing a semi-rigid connection within the multi-angle fastener.

12. The construct of claim 11, wherein the rotational movement of the upper and lower sections allows for a range of angulation in a range of about between 20–70 degrees relative to the central longitudinal axes of the upper and lower sections.

13. The construct of claim 10, wherein the mating surfaces include a pair of flat surfaces, said flat surfaces each forming an angle with the axes of the upper and lower sections when said axes are aligned, said flat surfaces angled to allow for a rotational movement of the upper and lower sections, with the pair of angled flat surfaces providing a rigid connection within the multi-angle fastener.

14. The construct of claim 13, wherein the flat surfaces are angled to allow for rotational movement in a range of about between 20–70 degrees relative to the central longitudinal axes of the upper and lower sections.

15. The construct of claim 10 further including a sleeve configured to surround the joint means for holding together the upper and lower sections at the joint means.

16. The construct of claim 15, wherein the sleeve is cylindrical in shape and includes an inner surface with threading on a portion of the inner surface, said sleeve threading engaging a threaded portion on the outer surface of the lower section of the fastener.

17. The construct of claim 10, wherein the series of fasteners includes at least two multi-angle fasteners.

18. The construct of claim 10, wherein the series of fasteners includes at least one bone bolt not capable of articulation.

19. An orthopedic construct comprising:
  a) a member with at least one attachment portion allowing attachment of a series of fasteners thereto at spaced apart positions along a length of each attachment portion;
  b) a series of fasteners attachable to said member at said at least one attachment portion, at least one of said fasteners including a multi-angle fastener having a pair of fasteners sections configured to be angled relative to one another;
  c) said multi-angle fastener comprising;
    an upper section having a central longitudinal axis, an externally threaded projection and an outer surface;
    a lower section having a central longitudinal axis and an outer surface having bone attachment means configured to be surgically implantable into a patient's bone tissue;
    joint means for connecting the upper and lower sections together, said joint means including corresponding mating surfaces configured to articulate with each other sufficiently to allow the upper and lower sections to angle relative to one another.

20. A multi-angle fastener for use in connecting a bone portion with a connecting member, said multi-angle fastener comprising:

a) an upper section having a central longitudinal axis, an externally threaded projection and an outer surface;
  b) a lower section having a central longitudinal axis and an outer surface having a bone attachment means configured to be surgically implantable into a patient's bone tissue; and
  c) joint means for connecting the upper and lower sections together, said joint means including corresponding mating surfaces configured to articulate with each other sufficiently to allow the upper and lower sections to angle relative to one another.

21. The fastener of claim 20, wherein the mating surfaces include corresponding concave and convex surfaces shaped to allow for a rotational movement of the upper and lower sections, with the corresponding concave and convex surfaces providing a semi-rigid connection within the multi-angle fastener.

22. The fastener of claim 21, wherein the rotational movement of the upper and lower sections allows for a range of angulation in a range of about between 20–70 degrees relative to the central longitudinal axes of the upper and lower sections.

23. The fastener of claim 20, wherein the mating surfaces include a pair of flat surfaces, said flat surfaces each forming an angle with the axes of the upper and lower sections when said axes are aligned, said flat surfaces angled to allow for a rotational movement of the upper and lower sections, with the pair of angled flat surfaces providing a rigid connection within the multi-angle fastener.

24. The fastener of claim 23, wherein the flat surfaces are angled to allow for rotational movement in a range of about between 20–70 degrees relative to the central longitudinal axes of the upper and lower sections.

25. The fastener of claim 20, further including a sleeve configured to surround the joint means for holding together the upper and lower sections at the joint means.

26. The fastener of claim 25, wherein the sleeve is cylindrical in shape and includes an inner surface with threading on a portion of the inner surface, said sleeve threading engaging a threaded portion on the outer surface of the lower section of the fastener.

* * * * *

EX PARTE REEXAMINATION CERTIFICATE (5412nd)

United States Patent
Bernhardt et al.

(10) Number: US 5,591,166 C1
(45) Certificate Issued: Jun. 20, 2006

(54) MULTI ANGLE BONE BOLT (75) Inventors: Andrew Bernhardt, Cordova, TN (US); Matthew M. Morrison, Memphis, TN (US)

(73) Assignee: Howmedica Osteonics Corp., Allendale, NJ (US)

Reexamination Request:
No. 90/005,212, Dec. 18, 1998

Reexamination Certificate for:
Patent No.: 5,591,166
Issued: Jan. 7, 1997
Appl. No.: 08/411,532
Filed: Mar. 27, 1995

(51) Int. Cl.
*A61B 17/56* (2006.01)

(52) U.S. Cl. .............................. 606/61; 606/60; 606/69; 606/72; 606/73

(58) Field of Classification Search .................. 606/60, 606/61, 72, 73, 69
See application file for complete search history.

(56) References Cited

U.S. PATENT DOCUMENTS

5,545,166 A * 8/1996 Howland ..................... 606/61
5,628,740 A * 5/1997 Mullane ..................... 606/61

* cited by examiner

*Primary Examiner*—David O. Reip (57) ABSTRACT

An orthopedic bone bolt and bone plate construct comprising a bone plate member and a series of fasteners. The bone plate member has at least one open portions, with the open portions allowing placement of a series of fasteners therethrough at spaced apart positions along a length of the open portions. The series of fasteners are attachable to the plate member at the open portions, with at least one of the fasteners including a multi-angle fastener having a pair of fastener sections configured to be angled relative to one another. The multi-angle fastener comprising; an upper section having a central longitudinal axis and an outer surface; a lower section having a central longitudinal axis and an outer surface with a threaded portion configured to be surgically implantable into a patient's bone tissue and a joint for connecting the upper and lower sections together. The joint including corresponding mating surfaces configured to articulate with each other sufficiently to allow the upper and lower sections to angle relative to one another.

US 5,591,166 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–9 is confirmed.

Claims 15 and 25 are cancelled.

Claims 10, 16, 19, 20 and 26 are determined to be patentable as amended.

Claims 11–14, 17, 18 and 21–24, dependent on an amended claim, are determined to be patentable.

New claims 27–39 are added and determined to be patentable.

10. An orthopedic bone bolt and spinal rod construct comprising:
   a) a spinal rod connected to a plurality of rod/bolt connectors, each connector having an open portion with each open portion allowing placement of a fastener therethrough, the connectors being at spaced apart positions along a length of the spinal rod; *and*
   b) a series of fasteners attachable to each of said connectors at each said connector open portion, at least one of said fasteners including a multi-angle fastener having a pair of fastener sections configured to be angled relative to one another;
   c) said multi-angle fastener comprising;
      an upper section having a central longitudinal axis, an externally threaded projection and an outer surface;
      a lower section having a central longitudinal axis and an outer surface having bone attachment means configured to be surgically implantable into a patient's bone tissue;
      joint means for connecting the upper and lower sections together, said joint means including corresponding mating surfaces *formed on the upper and lower sections, respectively, and* configured to articulate with each other sufficiently to allow the upper and lower sections to angle relative to one another*; and*
      *a sleeve configured to surround the joint means and engage the respective outer surfaces of the upper and lower sections to hold the joint means together.*

16. The construct of claim [15] *10*, wherein the sleeve is cylindrical in shape and includes an inner surface with threading on a portion of the inner surface, said sleeve threading *adapted for* engaging a threaded portion on the outer surface of the lower section of the fastener.

19. An orthopedic construct comprising:
   a) a member with at least one attachment portion allowing attachment of a series of fasteners thereto at spaced apart positions along a length of each attachment portion; *and*
   b) a series of fasteners attachable to said member at said at least one attachment portion, at least one of said fasteners including a multi-angle fastener having a pair of [fasteners] *fastener* sections configured to be angled relative to one another;
   c) said multi-angle fastener comprising;
      an upper section having a central longitudinal axis, an externally threaded projection, and an outer surface;
      a lower section having a central longitudinal axis and an outer surface having bone attachment means configured to be surgically implantable into a patient's bone tissue;
      joint means for connecting the upper and lower sections together, said joint means including corresponding mating surfaces *formed on the upper and lower sections, respectively, and* configured to articulate with each other sufficiently to allow the upper and lower sections to angle relative to one another*; and*
      *a sleeve configured to surround the joint means and engage the respective outer surfaces of the upper and lower sections to hold the joint means together.*

20. A multi-angle fastener for use in connecting a bone portion with a connecting member, said multi-angle fastener comprising:
   a) an upper section having a central longitudinal axis, an externally threaded projection and an outer surface;
   b) a lower section having a central longitudinal axis and an outer surface having a bone attachment means configured to be surgically implantable into a patient's bone tissue; [and]
   c) joint means for connecting the upper and lower sections together, said joint means including corresponding mating surfaces *formed on the upper and lower sections, respectively, and* configured to articulate with each other sufficiently to allow the upper and lower sections to angle relative to one another*; and*
   *d) a sleeve configured to surround the joint means and engage the respective outer surfaces of the upper and lower sections to hold the joint means together.*

26. The fastener of claim [25] *20*, wherein the sleeve is cylindrical in shape and includes an inner surface with threading on a portion of the inner surface, said sleeve threading *adapted for* engaging a threaded portion on the outer surface of the lower section of the fastener.

27. *An orthopedic bone bolt and spinal rod construct comprising:*
   a) *a spinal rod connected to a plurality of rod/bolt connectors, each connector having an open portion with each open portion allowing placement of a fastener therethrough, the connectors being at spaced apart positions along a length of the spinal rod; and*
   b) *a series of fasteners attachable to each of said connectors at each said connector open portion, at least one of said fasteners including a multi-angle fastener having a pair of fastener sections configured to be angled relative to one another;*
   c) *said multi-angle fastener including;*
      i) *an upper section having a central longitudinal axis, an externally threaded projection and an outer surface;*
      ii) *a lower section having a central longitudinal axis and an outer surface having bone attachment means configured to be surgically implantable into a patient's bone tissue; and*
      iii) *joint means for connecting the upper and lower sections together, said joint means including corre-* sponding mating surfaces configured to articulate with each other sufficiently to allow the upper and lower sections to angle relative to one another, wherein the mating surfaces include a pair of flat surfaces, said flat surfaces each forming an angle with the axes of the upper and lower sections when the axes are aligned, said flat surfaces angled to allow for a rotational movement of the upper and lower sections, with the pair of angled flat surfaces providing a rigid connection within the multi-angle fastener.

28. The construct of claim 27, wherein the flat surfaces are angled to allow for rotational movement in a range of about between 20–70 degrees relative to the central longitudinal axes of the upper and lower sections.

29. An orthopedic bone bolt and spinal rod construct comprising:
   a) a spinal rod connected to a plurality of rod/bolt connectors, each connector having an open portion with each open portion allowing placement of a fastener therethrough, the connectors being at spaced apart positions along a length of the spinal rod; and
   b) a series of fasteners attachable to each of said connectors at each said connector open portion, at least one of said fasteners including a multi-angle fastener having a pair of fastener sections configured to be angled relative to one another;
   c) said multi-angle fastener including;
      i) an upper section having a central longitudinal axis, an externally threaded projection and an outer surface;
      ii) a lower section having a central longitudinal axis and an outer surface having bone attachment means configured to be surgically implantable into a patient's bone tissue;
      iii) joint means for connecting the upper and lower sections together, said joint means including corresponding mating surfaces configured to articulate with each other sufficiently to allow the upper and lower sections to angle relative to one another; and
      iv) a sleeve configured to surround the joint means for holding together the upper and lower sections at the joint means, wherein the sleeve is cylindrical in shape and includes an inner surface with threading on a portion of the inner surface, said sleeve threading engaging a threaded portion on the outer surface of the lower section of the fastener.

30. A multi-angle fastener for use in connecting a bone portion with a connecting member, said multi angle fastener comprising:
   a) an upper section having a central longitudinal axis, an externally threaded projection and an outer surface;
   b) a lower section having a central longitudinal axis and an outer surface having bone attachment means configured to be surgically implantable into a patient's bone tissue; and
   c) joint means for connecting the upper and lower sections together, said joint means including corresponding mating surfaces configured to articulate with each other sufficiently to allow the upper and lower sections to angle relative to one another, wherein the mating surfaces include a pair of flat surfaces, said flat surfaces each forming an angle with the axes of the upper and lower sections when said axes are aligned, said flat surfaces angles to allow for a rotational movement of the upper and lower sections, with the pair of angled flat surfaces providing a rigid connection within the multi angle fastener.

31. The fastener of claim 30, wherein the flat surfaces are angled to allow for rotational movement in a range of about between 20–70 degrees relative to the central longitudinal axes of the upper and lower sections.

32. The fastener of claim 30, further including a sleeve configured to surround the joint means for holding together the upper and lower sections at the joint means.

33. The fastener of claim 32, wherein the sleeve is cylindrical in shape and includes an inner surface with threading on a portion of the inner surface, said sleeve threading engaging a threaded portion on the outer surface of the lower section of the fastener.

34. A multi-angle fastener for use in connecting a bone portion with a connecting member, said multi angle fastener comprising:
   a) an upper section having a central longitudinal axis, an externally threaded projection and an outer surface;
   b) a lower section having a central longitudinal axis and an outer surface having bone attachment means configured to be surgically implantable into a patient's bone tissue; and
   c) joint means for connecting the upper and lower sections together, said joint means including corresponding mating surfaces configured to articulate with each other sufficiently to allow the upper and lower sections to angle relative to one another; and
   d) a sleeve configured to surround the joint means for holding together the upper and lower sections at the joint means, wherein the sleeve is cylindrical in shape and includes an inner surface with threading on a portion of the inner surface, said sleeve threading engaging a threaded portion on the outer surface of the lower section of the fastener.

35. An orthopedic bone bolt and spinal rod construct comprising:
   a) a spinal rod connected to a plurality of rod/bolt connectors, each connector having an open portion with each open portion allowing placement of a fastener therethrough, the connectors being at spaced apart positions along a length of the spinal rod; and
   b) a series of fasteners attachable to each of said connectors at each said connector open portion, at least one of said fasteners including a multi-angle fastener having a pair of fastener sections configured to be angled relative to one another;
   c) said multi-angle fastener comprising:
      i) an upper section having a central longitudianl axis, an externally threaded projection and an outer surface;
      ii) a lower section having a central longitudinal axis and an outer surface having bone attachment means configured to be surgically implantable into a patient's bone tissue; and
      iii) joint means for connecting the upper and lower sections together, said joint means including corresponding mating surfaces formed on the upper and lower sections, respectively, and configured to articulate with each other sufficiently to allow the upper and lower sections to angle relative to one another, wherein the mating surfaces include a pair of flat surfaces, said flat surfaces each forming an angle with the axes of the upper and lower sections when the axes are aligned, said flat surfaces angled to allow for rotational movement of the upper and

*lower sections, with the pair of angled flat surfaces providing a rigid connection within the multi-angle fastener.*

*36. The construct of claim 35, wherein the flat surfaces are angled to allow for rotational movement in the range of about between 20–70 degrees relative to the central longitudinal axes of the upper and lower sections.*

*37. The construct of claim 35, wherein the flat surfaces are angled to allow for rotational movement in the range of about between 20–70 degrees relative to the central longitudinal axes of the upper and lower sections.*

*38. The construct of claim 35, further including a sleeve configured to surround the joint means for holding together the upper and lower sections at the joint means.*

*39. A multi-angle fastener for use in connecting a bone portion with a connecting member, said multi-angle fastener comprising:*

*a) an upper section having a central longitudinal axis, an externally threaded projection and an outer surface;*

*b) a lower section having a central longitudinal axis and an outer surface having bone attachment means configured to be surgically implantable into a patient's bone tissue;*

*c) joint means for connecting the upper and lower sections together, said joint means including corresponding mating surfaces formed on the upper and lower sections, respectively, and configured to articulate with each other sufficiently to allow the upper and lower sections to angle relative to one another, wherein the mating surfaces include a pair of flat surfaces, said flat surfaces each forming an angle with the axes of the upper and lower sections when said axes are aligned, said flat surfaces angled to allow for a rotational movement of the upper and lower sections, with the pair of angled flat surfaces providing a rigid connection within the multi-angle fastener.*

\* \* \* \* \*